United States Patent [19]

Gnerlich et al.

[11] Patent Number: 4,571,556
[45] Date of Patent: Feb. 18, 1986

[54] RANDOMIZED-CLOCK CIRCUIT

[75] Inventors: Hans R. Gnerlich, Bethlehem, Pa.; Kuno P. Zimmermann, Kansas City, Mo.

[73] Assignee: MI Medical & Scientific Instruments, Inc., Bethlehem, Pa.

[21] Appl. No.: 517,969

[22] Filed: Jul. 28, 1983

[51] Int. Cl.⁴ .................. H03B 29/00; A61N 1/32
[52] U.S. Cl. .................... 331/78; 128/421; 364/717
[58] Field of Search ............ 331/78; 364/717; 128/420 A, 421, 422, 423 W

[56] References Cited

U.S. PATENT DOCUMENTS

| | | | |
|---|---|---|---|
| 3,492,587 | 1/1970 | Hutton | 331/78 X |
| 3,609,327 | 9/1971 | Paine et al. | 340/348 X |
| 3,691,472 | 9/1972 | Bohman | 331/78 X |
| 3,961,169 | 6/1976 | Bishop et al. | 331/78 X |
| 4,213,101 | 7/1980 | Policand et al. | 331/78 |
| 4,296,384 | 10/1981 | Mishima | 331/78 |

OTHER PUBLICATIONS

Lancaster, "CMOS Cookbook", Howard W. Sams, Co. Inc., 1977, pp. 320-323.
Buron et al., "Noise Generated by Digital Technique", IBM Disclosure Bulletin, vol. 8, No. 9, Feb. 1966, p. 1232.

Primary Examiner—Siegfried H. Grimm

[57] ABSTRACT

A randomized-clock circuit produces a random pulse train of predetermined sequence length and truncated exponential distribution of the gaps between pulses by multiplying a periodic clock signal with the output signal of a maximal length pseudorandom sequence generator which is clocked by the periodic clock signal. Control circuits monitor the maximal length pseudorandom pulse generator to start or stop random pulse sequences; random sequences are repeatable and a circuit to preset their starting point is provided. Cascading or connecting randomized-clock circuits in XOR, OR or AND gates is used to change the parameters of the exponential distribution function of the gaps. Pulse width and amplitude adjusting circuits allow interfacing of the randomized-clock circuit (a) with trigger inputs of medical and scientific pulse generators and (b) with electrodes connected to primates when the randomized-clock circuit is used as a nerve and/or muscle stimulator.

9 Claims, 9 Drawing Figures

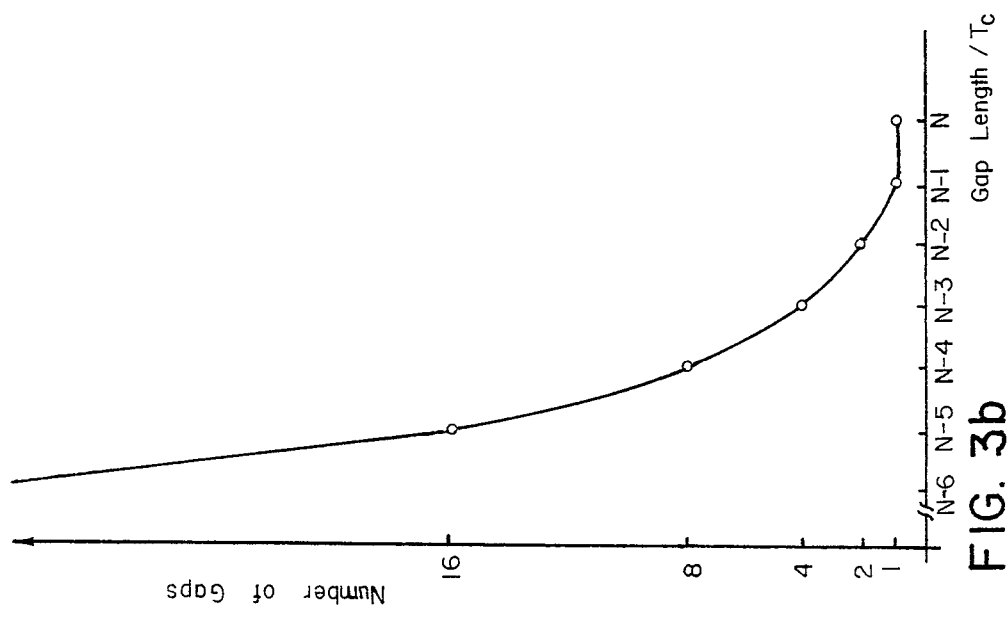
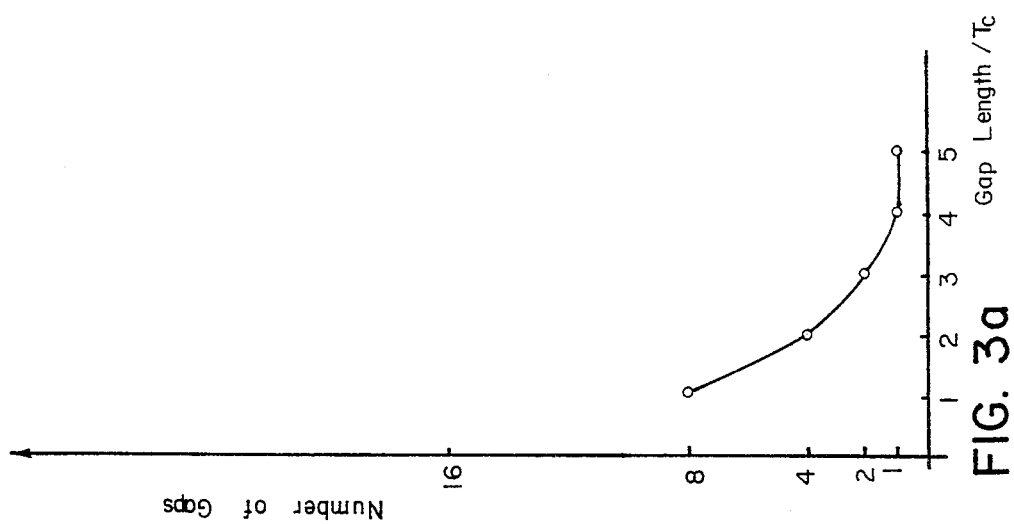

RANDOMIZED-CLOCK CIRCUIT

BACKGROUND OF THE INVENTION

1. Field of the Invention

The present invention relates to maximal length pseudorandom pulse generating circuits, and more particularly, to a circuit producing trains of pulses of predetermined random sequence length and known statistical distribution function of the occurrence of the gaps between the random sequence pulses.

2. Description of Prior Art

Maximal length pseudorandom sequence generators using synchronously clocked shift registers produce strings of rectangular pulses, where period and width are both randomly varying, and the gap statistics does not obey a truncated exponential distribution function. The maximal sequence length is determined by an irreducible polynomial over the Galois field of $2^N$ elements and is implemented with N shift register stages and mod-2 feedback connections as required by the polynomial.

Computer programs and pseudorandom number generators with known gap statistics, designed to fulfill specific requirements, are too expensive to manufacture and/or impractical for reliability simulations, random samplers, random evoked potential measurements, random x-y position generators for use in battle field simulations and video games, identification of unknown systems, nerve and muscle stimulation, etc.

OBJECTS AND SUMMARY OF THE INVENTION

It is the primary object of the present invention to provide inexpensive, practical and simple methods and circuits to generate a train of pulses, occurring at random, integer multiples of a clock period, where clock period, pulse width and/or pulse amplitude are adjustable. The distribution of the gaps in the pulse train will satisfy a truncated exponential law and the train of random pulses will repeat in the same order every time the string will start over.

Another object of the present invention is to provide a "clock randomizer" to produce a train of pulses according to the primary object from a periodic clock signal, where cascading clock randomizers and combining randomized-clock circuits in XOR, OR or AND gates improves the quality of randomness.

A further object of the present invention is to provide a random trigger circuit to produce a train of pulses according to the primary or secondary object, where pulse width and/or pulse amplitude are adjustable. Presently existing medical and scientific pulse generators can then be modified with this invention, easily and inexpensively, to produce pseudorandom pulse trains, required for example, in the measurement of random evoked potentials.

Still a further object is to provide a random electrical nerve and/or muscle stimulator to produce a train of stimulating pulses according to the primary or secondary object, where pulse width and/or pulse amplitude are adjustable, for example, to improve the pain control effectiveness of Transcutaneous Electrical Nerve Stimulators (TENS).

These and other objects of the invention are achieved by multiplying a periodic clock signal with the output signal of a maximal length pseudorandom sequence generator, which is clocked by the periodic clock signal.

The output of the multiplier is a pulse train with a gap distribution function equal to a truncated exponential distribution function; conventional pseudorandom sequence generators don't exhibit this characteristic. However, the mean gap is always two, independent of the random sequence. Cascading a randomized-clock circuit with R, R=1, 2, . . . , clock randomizers produces mean gaps equal to $2^{R+1}$.

Combining randomized-clock circuits in logic XOR, OR or AND gates also improves the means gap value. The random pulse sequences have exponential distribution functions of the gaps and modulation of the pulse width when clock frequencies of the individual randomized-clock circuits are slightly different.

When the pulse width is adjusted to approach zero (impulse), or in practice, to less than one tenth of the clock period, then the output of the randomized-clock circuit approaches a truncated Poisson sequence. Commercial applications for inexpensive Poisson generators are in communications, control, medicine, psychology and military science.

The technical simplicity and wide applications of the invention will be discussed hereafter in detail. The novel features of the invention are set forth in detail in the appended claims. The invention will be best understood from the following description of preferred embodiments, when read in conjunction with the accompanying drawings.

BRIEF DESCRIPTION OF THE DRAWINGS

FIGS. 3a and 3b are graphs useful in explaining the statistics of the novel pseudorandom pulse trains;

DESCRIPTION OF THE PREFERRED EMBODIMENTS

The invention will now be described in detail with examples, without the intention of restricting the invention to these examples.

Figure 1:
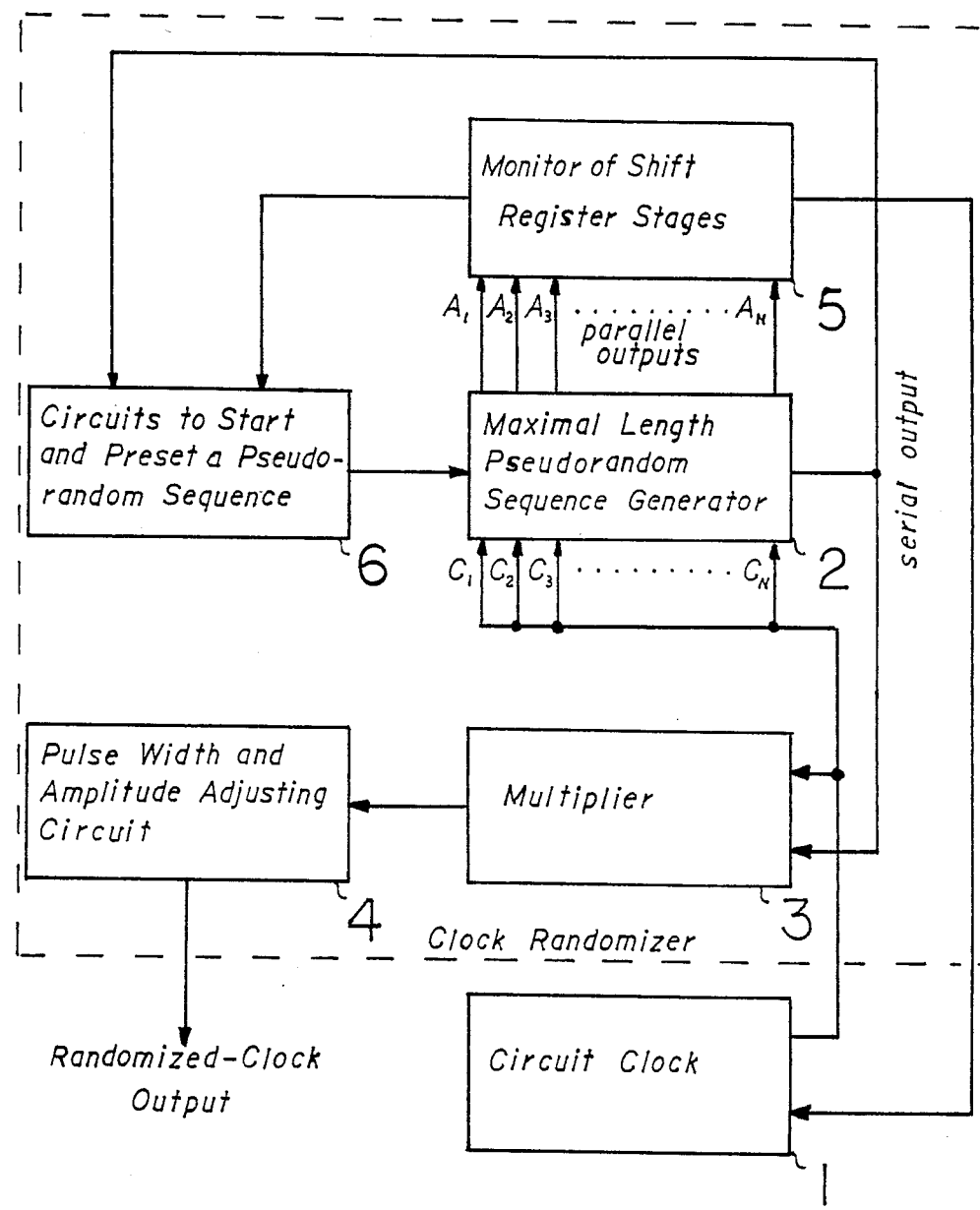
FIG. 1 is a block diagram of the novel randomized-clock circuit of the present invention.

It should be appreciated that various circuit design techniques may be used in the implementation of the logic, switching and control circuits, which are therefore shown in block form. Reference is now made to FIG. 1, which is a generalized block diagram of a preferred embodiment of the randomized-clock circuit of this invention.

1 is the circuit clock, 2 the maximal length pseudorandom sequence generator, 3 the multiplier, 4 the pulse width and amplitude adjusting circuit, 5 the monitor of the shift register stages, and 6 the circuit to start and/or preset the maximal length pseudorandom sequence generator 2. The circuit clock 1 is connected to (a) the clock terminals $C_1, C_2, \ldots C_N$ of the maximal length pseudorandom sequence generator 2 and (b) one input terminal of the multiplier 3. The serial output of the maximal length pseudorandom sequence generator 2 is connected to (a) the second input of the multiplier 3 and (b) one input terminal of the circuit to start and/or preset a random sequence 6. The output of the multiplier 3 is connected to the input of the pulse width and amplitude adjusting circuit 4. The parallel outputs $A_1$, $A_2$, ... $A_N$ of the maximal length pseudorandom sequence generator 2 are connected to the monitor of the shift register stages 5. One output of the monitor 5 is connected to the second input of the circuit to start and/or preset a random sequence 6, which is connected to the maximal length pseudorandom sequence generator 2. The other output of monitor 5 is connected to the input of the circuit clock 1.

Circuit Clock 1: Any circuit or device that produces pulses of constant width, period and amplitude can be used, as long as the pulse amplitude, frequency and width satisfy the specifications of the multiplier and maximal length pseudorandom sequence generator. An astable multivibrator IC with fifty percent duty cycle and with an output enable is a preferred example for a free running clock.

Maximal Length Pseudorandom Sequence Generator 2: Examples of pseudorandom sequence generator circuits using synchronously clocked shift registers and generating random sequences up to $2^{31}-1$ clock pulses long are listed by D. Lancaster, CMOS Cookbook, Howard W. Sams, Co. Inc., 1977.

Multiplier 3: Any device or circuit permitting multiplication of two signals may be used. An AND gate is a preferred choice for a multiplier of this invention.

Pulse Width and Amplitude Adjusting Circuit 4: A circuit or device permitting adjustments of the pulse width W of the amplitude modulator output signal between $W = \Delta W$, where $\Delta W \rightarrow 0$, and $W = T_C$, where $T_C$ is the period of the clock pulse. A triggered monostable vibrator IC with variable resistor and capacitor to change the duty cycle is a preferred example implementing the pulse width adjusting circuit. For adjusting the amplitude, voltage dividers, multipliers and transformers may be used.

Monitor of Shift Register Stages 5: Upon power-up all N register stages will arbitrarily settle in a high or low state, which may be displayed with LEDs. Any register setting, except all zeros, which will bring the generation of a series to a halt, is permissible. A logic circuit, implementing $A_1 + A_2 + \ldots A_N$, monitors all register stages. Its output is a logic 1 if all register stages are simultaneously zero, and is a logic 0 otherwise. Other logic circuits may be added to monitor the register stages and set flags or stop the circuit clock when certain high or low register stage states are obtained.

Circuits to Start and/or Preset a Pseudorandom Sequence 6: Combining monitor and serial outputs in a logic OR operation and entering the resulting signal at the register stage one input of the maximal length pseudorandom sequence generator 2 will automatically start a halted sequence, if and only if the illegal zero condition exists and will not interfere with normal serial output feedback. If a monitor is not used and a pseudorandom series with exact statistics is not required, then a resistor-capacitor start-up circuit, as described by Lancaster, may be used, if any.

To preset a pseudorandom sequence to a specific starting word, the serial output feedback to the input of register stage one is disabled The circuit clock is switched to manual and the desired serial word is entered at the input of register stage one and shifted into position with the manually operated clock. The serial output feedback to the input of register stage one is enabled and the clock switched to auto to start the generation of the maximal length pseudorandom pulse sequence from the specific starting word.

Figure 2A:
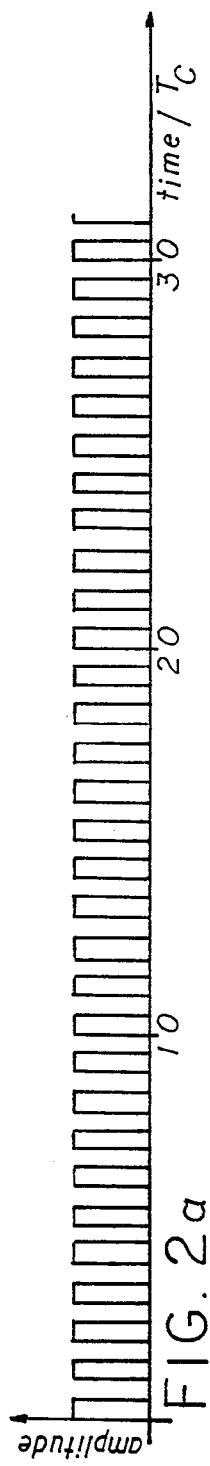
FIGS. 2a, 2b, 2c and 2d show the output of the circuit clock, pseudorandom sequence generator, pulse and impulse generating circuit, respectively.
Figure 2B:
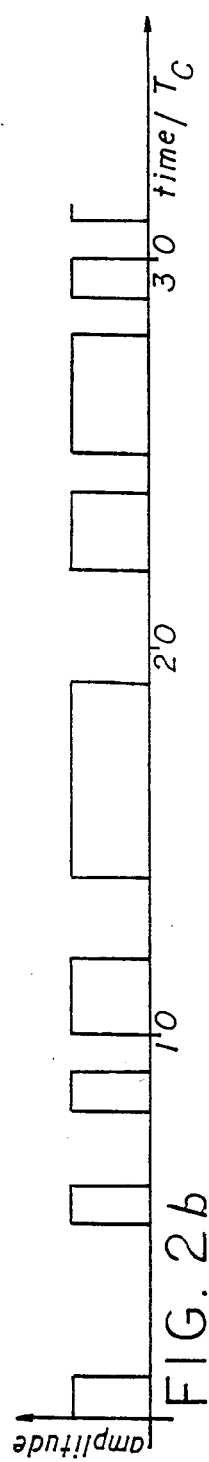
Figure 2C:
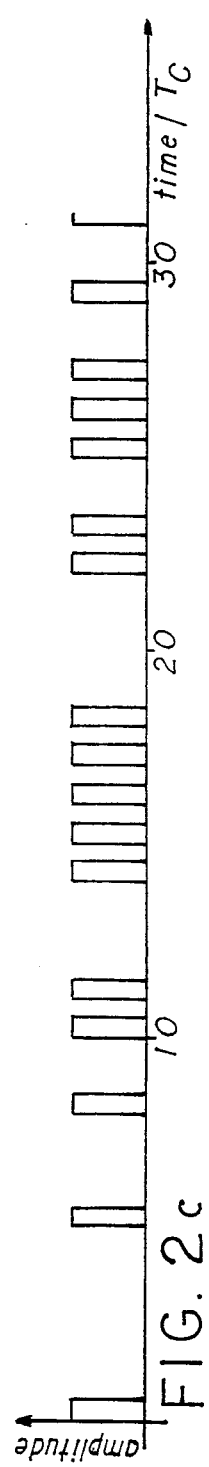
Figure 2D:
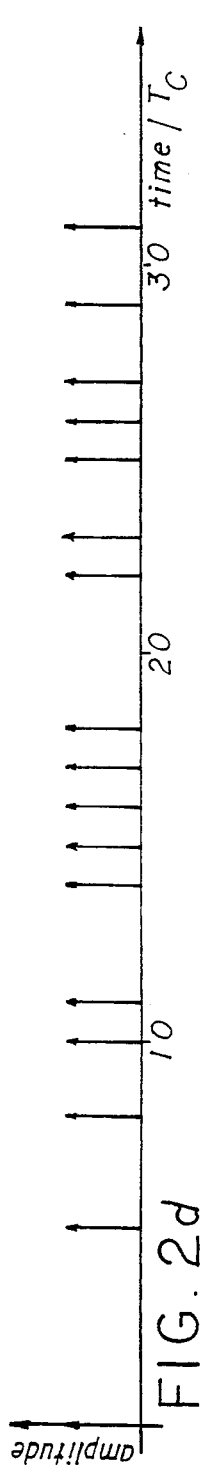

Example: A five stage maximal length pseudorandom sequence generator produces a random pulse sequence that is $2^5 - 1 = 31$ clock periods long. After 31 clock periods the series repeats itself. FIG. 2a shows the clock pulses, FIG. 2b the maximal length pseudorandom sequence, FIG. 2c the randomized-clock pulses at the output of the amplitude modulator, and FIG. 2d the truncated Poisson sequence obtainable at the pulse width and amplitude adjusting circuit output. The statistics of the gap distribution is as follows: There are $2^{(N-1)-i}$ gaps equal to i clock periods, where $1 \leq i \leq N-1$, plus one gap equal to N clock periods. $2^N - 1$ is the maximal length of the pseudorandom sequence and N is the number of stages. The gap distribution is shown in FIG. 3a for the 5-stage and in FIG. 3b for an N-stage randomized-clock circuit. The mean gap is equal to two, independent of the number of stages.

In applied science, engineering and medicine, signals with known random properties are desired for:

1. Identification of unknown systems by exciting the input(s) with random signals and analazing the output(s) using correlation methods to determine the parameters of the unknown system.

2. Prevention or hindrance of information transmission, as in radar or radio jamming, or blocking of nerve electrical activity for pain control.

3. Random excitation of systems with memory capability to eliminate stimulus learning.

We have invented circuits to generate trains of pulses of arbitrary shape, occurring at random integer multiples of a clock period. The clock period is adjustable. The distribution of the gaps satisfies a truncated exponential law. When set to generate rectangular pulses, the pulse width can, in addition, be adjusted to produce in the limits (a) pulse width=clock period, a pseudorandom pulse train or (b) pulse width→0, a Poisson impulse train.

Triggering a standard, commercially available pulse generator with a randomized-clock circuit of this invention will upgrade the generator to produce, in addition to standard pulses, random pulse sequences.

A randomized-clock circuit with pulse width and/or amplitude adjusting circuitry connected to electrodes which are attached or implanted to a human or animal body comprises a novel random pulse generator for nerve and/or muscle stimulation. Superior pain control and the elimination of stimulus learning is achieved using the random pulse generator of this invention as a nerve stimulator, compared to presently used periodic or burst pulse stimulators. In a random stimulator of this invention the power amplitude distribution is continuous. Almost all nerve fibers in a pain (treatment) area are concurrently stimulated and optimum pain blockage and relief of pain are achieved. Because the random nature of the signal prevents accomodation, in long term treatment maximum pain relief is obtained at lower power levels, minimizing the possibility of electrode burn, discomfort, spasm or tetany.

Autostart, preset and load, or set flag and stop random sequence features, added to the randomized-clock circuit of this invention, allow the repeated application of identical, truncated random pulse sequences to unknown systems for identification or for random evoked potential measurements.

Figure 4:
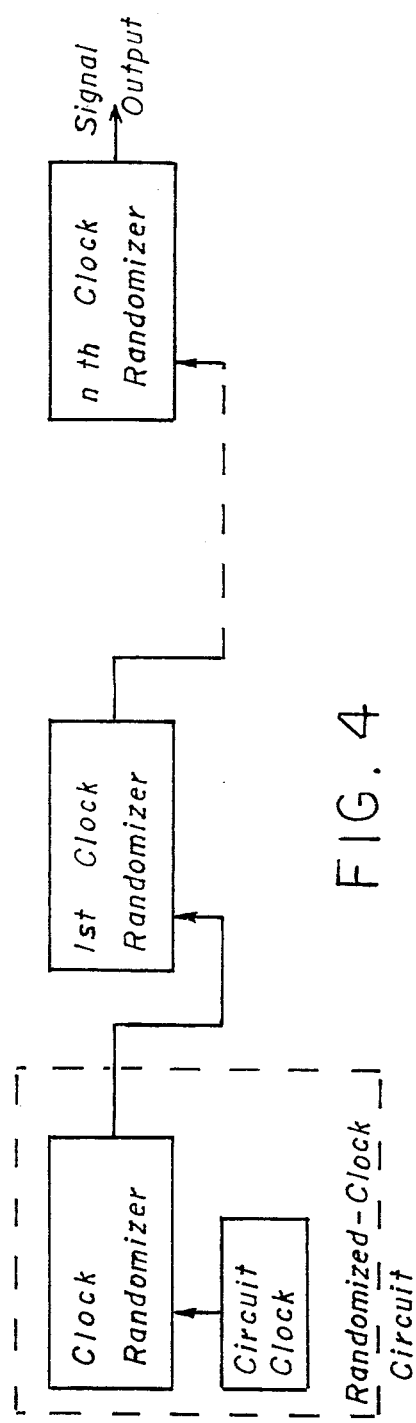
FIG. 4 is a block diagram of a cascaded randomized-clock circuit.

Cascaded randomized-clock circuits, see FIG. 4, can be used to produce Poisson pulse sequences with mean gaps equal to $2^C$, where C is the number of cascaded randomized-clock circuits. When digital signal processing of random sequences of this invention is required to verify and evaluate experimental results, cascades of several randomized-clock circuits may be required to produce random pulse sequences, which simulate ideal Poisson pulse sequences. The spectral analysis of a Poisson sequence generated with four cascaded randomized-clock circuits of this invention did not reveal the synthetic origin, when compared to an ideal Poisson pulse sequence.

Figure 5:
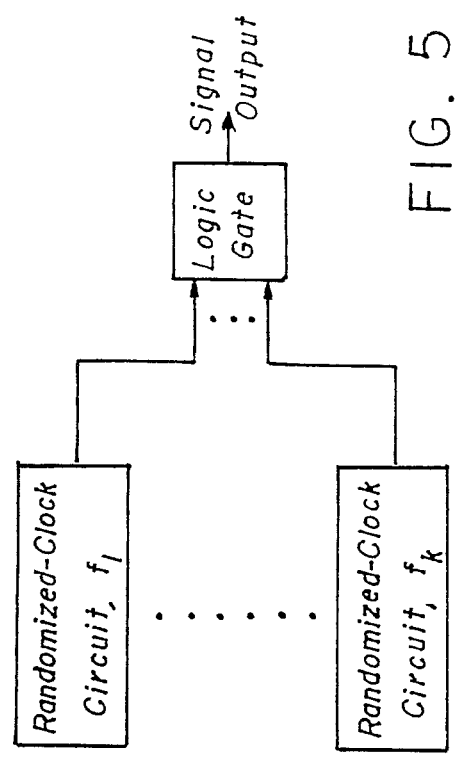
FIG. 5 is a block diagram of randomized-clock circuits combined in XOR, OR or AND logic gates.

Combining randomized-clock circuits in logic XOR, OR, and AND gates, see FIG. 5, produces random pulse sequences with various exponential distribution functions of the gaps and modulation of the pulse width, when clock frequencies are slightly different. The application of these random pulse generators in hindrance of information transmission, pain control and muscle stimulation has provided results, which, although unexpected, proved their effectiveness compared to the presently used periodic and burst stimulators.

Although particular embodiments of the invention have been described and illustrated herein, it is recognized that modifications and variations may readily occur to those skilled in the art and consequently, it is intended that the claims be interpreted to cover such modifications and equivalents

What is claimed is:

1. A randomized-clock circuit comprising a maximal length pseudorandom sequence generator (MLPSG), a periodic circuit clock, a multiplier, a circuit to start a pseudorandom sequence and a pulse width and amplitude adjusting circuit, the multiplier, multiplying the output of the MLPSG with the output of the periodic circuit clock, is providing at its output a random pulse train of known sequence length and gap statistics with truncated exponential distribution, the MLPSG comprises an N-stage shift register, selected stages of which are mod-2 fed back to the input of the MLPSG, wherein the feedback satisfies a primitive, irreducible polynominal of degree N, the circuit to start a psueudorandom sequence is sending a starting pulse to the MLPSG if the MLPSG is in a state in which it does not produce pulse sequences, the pulse width and amplitude adjusting circuit is regulating the width, amplitude, shape and power of the pulses of the random sequence.

2. A randomized-clock circuit, as recited in claim 1, wherein a circuit to preset the maximal length pseudorandom sequence generator to a specific starting value is provided and a monitor and control circuit is provided to selectively (a) stop the circuit clock and (b) indicate when a certain combination of high and low states of the shift register stages is detected.

3. A randomized-clock circuit, as recited in claim 1, wherein the output of the pulse width and amplitude adjusting circuit is making contact with a primate body through electrodes for nerve and muscle stimulation.

4. A cascaded randomized-clock circuit, wherein a randomized-clock circuit is the circuit clock for n, n=1, 2, ..., cascaded clock randomizers, said randomized-clock circuit comprising a maximal length pseudorandom sequence generator (MLPSG), a periodic circuit clock, a multiplier, a circuit to start a pseudorandom sequence and a pulse width and amplitude adjusting circuit, the multiplier, multiplying the output of the MLPSG with the output of the periodic circuit clock, is providing at its output a random pulse train of known sequence length and gap statistics with truncated exponential distribution, the MLPSG comprises an N-stage shift register, selected stages of which are mod-2 fed back to the input of the MLPSG, wherein the feedback satisfied a primitive, irreducible polynomial of degree N, the circuit to start a pseudorandom sequence is sending a starting pulse to the MLPSG is in a state in which it does not produce pulse sequences, the pulse width and amplitude adjusting circuit is regulating the width, amplitude, shape and power of the pulses of the random sequence.

5. A cascaded randomized-clock circuit, as recited in claim 4, wherein a circuit to preset the maximal length pseudorandom sequence generator to a specific starting value is provided and a monitor and control circuit is provided to selectively (a) stop the circuit clock and (b) indicate when a certain combination of high and low states of the shift register stages is detected.

6. A cascaded randomized-clock circuit, as recited in claim 4, wherein the output of the pulse width and amplitude adjusting circuit of the cascade's last clock randomizer makes contact with a primate body through electrodes for nerve and muscle stimulation.

7. A random pulse generator comprising k randomized-clock circuits with periodic clock frequencies $f_k = f_{k-1} + \Delta f_k$, $f_k >> \Delta f_k$, where $k = 2, 3, \ldots$, and the randomized-clock circuit outputs are combined in one of a XOR, OR and AND gate, said randomized-clock circuit comprising a maximal length pseudorandom sequence generator (MLPSG), a periodic circuit clock, a multiplier, a circuit to start a pseudorandom sequence and a pulse width and amplitude adjusting circuit, the multiplier, multiplying the output of the MLPSG with the output of the periodic circuit clock, is providing at its output a random pulse train of known sequence length and gap statistics with truncated exponential distribution, the MLPSG comprises an N-stage shift register, selected stages of which are mod-2 fed back to the input of the MLPSG, wherein the feedback satisfies a primitive, irreducible polynomial of degree N, the circuit to start a pseudorandom sequence is sending a starting pulse to the MLPSG if the MLPSG is in a state in which it does not produce pulse sequences, the pulse width and amplitude adjusting circuit is regulating the width, amplitude, shape, and power of the pulses of the random sequence.

8. A random pulse generator, as recited in claim 7, wherein circuits to preset the maximal length pseudorandom sequence generators to a specific starting value are provided.

9. A random pulse generator, as recited in claim 7, wherein the output of the logic gate, after being amplitude and pulse width adjusted, is making contact with a primate body through electrodes for nerve and muscle stimulation.

* * * * *